United States Patent [19]
Rosen et al.

[11] Patent Number: 5,141,905
[45] Date of Patent: * Aug. 25, 1992

[54] DNA SEQUENCES ENCODING BMP-7 PROTEINS

[76] Inventors: Vicki A. Rosen, 127 Kilsyth Rd., Brookline, Mass. 02146; Elizabeth A. Wang, 136 Wolf Rock Rd., Carlisle, Mass. 01741; John M. Wozney, 59 Old Bolton Rd., Hudson, Mass. 01749

[*] Notice: The portion of the term of this patent subsequent to Apr. 21, 2009 has been disclaimed.

[21] Appl. No.: 438,919

[22] Filed: Nov. 17, 1989

Related U.S. Application Data

[63] Continuation-in-part of Ser. No. 370,549, Mar. 23, 1989, abandoned, which is a continuation-in-part of Ser. No. 347,559, May 4, 1989, abandoned, and a continuation-in-part of Ser. No. 329,610, Mar. 28, 1989, abandoned, which is a continuation-in-part of Ser. No. 179,100, Apr. 8, 1988, Pat. No. 5,013,649, and Ser. No. 179,101, Apr. 8, 1988, and Ser. No. 179,197, Apr. 8, 1988, each is a continuation-in-part of Ser. No. 28,285, Mar. 20, 1987, abandoned, and Ser. No. 31,346, Mar. 26, 1987, Pat. No. 4,877,864, each is a continuation-in-part of Ser. No. 943,332, Dec. 17, 1986, abandoned, and Ser. No. 880,776, Jul. 1, 1986, abandoned.

[51] Int. Cl.$^5$ .................. C12P 21/02; C12P 19/34; C12N 15/00; C12N 7/00; C12N 5/00; C12N 1/21; C12N 1/16; C12N 1/18; C07K 3/00; C07H 15/12

[52] U.S. Cl. .................. 435/69.1; 435/91; 435/172.3; 435/235.1; 435/320.1; 435/240.1; 435/252.3; 435/255; 435/256; 536/27; 530/350; 935/18; 935/27; 935/31; 935/34; 935/38; 935/55; 935/62; 935/70; 935/72; 935/81

[58] Field of Search .................. 435/69.1, 91, 172.3, 435/235, 240.1, 252.3, 320.1, 255, 256, 235.1; 536/27; 530/350; 935/18, 27, 31, 38, 34, 55, 62, 70, 72, 81

[56] References Cited

PUBLICATIONS

Wozney et al. Science vol. 242 pp. 1528–1534 (1988).

*Primary Examiner*—Joan Ellis
*Attorney, Agent, or Firm*—Ellen J. Kapinos; Bruce M. Eisen

[57] ABSTRACT

Purified BMP-7 proteins and processes for producing them are disclosed. The proteins may be used in the treatment of bone and/or cartilage defects and in wound healing and related tissue repair.

17 Claims, 7 Drawing Sheets

FIGURE 1

1   TCTAGAGGTGAGAGCAGCCAACAAGAGAAAAAATCAAAACCGCAATAAATCCGGCTCTCAT   61
    LeuGluValArgAlaAlaAsnLysArgLysAsnGlnAsnArgAsnLys<u>SerGlySerHis</u>
    (1)                                                     (15)

62  CAGGACTCCTCTAGAATGTCCAGTGTTGGAGATTATAACACCAGTGAACAAAAACAAGCC   121
    <u>GlnAspSerSerArg</u>MetSerSerValGlyAspTyrAsnThrSerGluGlnLysGlnAla
                (23)

122 TGTAAAAAGCATGAACTCTATGTGAGTTTCCGGGATCTGGGATGGCAGGACTGGATTATA   181
    CysLysLys<u>HisGluLeuTyrValSerPhe</u>ArgAspLeuGlyTrpGlnAspTrpIleIle (42)

182 GCACCAGAAGGATATGCTGCATTTTATTGTGATGGAGAATGTTCTTTTCCACTCAATGCC   241
    AlaProGluGlyTyrAlaAlaPheTyrCysAspGlyGluCysSerPheProLeuAsnAla

242 CATATGAATGCCACCAATCATGCCATAGTTCAGACTCTGGTTCACCTGATGTTTCCTGAC   301
    HisMetAsnAlaThrAsnHisAlaIleValGlnThrLeuValHisLeuMetPheProAsp

302 CACGTACCAAAGCCTTGCTGCGCGACAAACAAACTAAATGCCATCTCTGTGTTGTACTTT   361
    HisValProLysProCysCysAlaThrAsnLysLeuAsnAlaIleSerValLeuTyrPhe

362 GATGACAGCTCCAATGTCATTTTGAAAAAGTACAGAAATATGGTCGTGCGTTCGTGTGGT   421
    AspAspSerSerAsnValIleLeuLysLysTyrArgAsnMetValValArgSerCysGly

422 TGCCACTAATAGTGCATAATAATGGTAATAAGAAAAAAGATCTGTATGGAGGTTTATGA   481
    CysHisEnd
        (140)

481 CTACAATAAAAAATATCTTTCGGATAAAAGGGGAATTTAATAAAATTAGTCTGGCTCATT   540

541 TCATCTCTGTAACCTATGTACAAGAGCATGTATATAGT   578

FIGURE 2

```
            9              18              27              36              45              54
CTG CTG GGC ACG CGT GCT GTG TGG GCC TCA GAG GCG GGC TGG CTG GAG TTT GAC
Leu Leu Gly Thr Arg Ala Val Trp Ala Ser Glu Ala Gly Trp Leu Glu Phe Asp
(1)
            63             72              81              90              99             108
ATC ACG GCC ACC AGC AAC CTG TGG GTC CTG ACT CCG CAG CAC AAC ATG GGG CTG
Ile Thr Ala Thr Ser Asn Leu Trp Val Leu Thr Pro Gln His Asn MET Gly Leu 117            126             135             144             153             162
CAG CTG AGC GTG GTC ACG CGT GAT GGG CTC AGC ATC AGC CCT GGG GCC GCG GGC
Gln Leu Ser Val Val Thr Arg Asp Gly Leu Ser Ile Ser Pro Gly Ala Ala Gly 171            180             189             198             207             216
CTG GTG GGC AGG GAC GGC CCC TAC GAC AAG CAG CCC TTC ATG GTG GCC TTC TTC
Leu Val Gly Arg Asp Gly Pro Tyr Asp Lys Gln Pro Phe MET Val Ala Phe Phe 225            234             243             252             261             270
AAG GCC AGT GAG GTC CAC GTG CGC AGT GCC CGG TCG GCC CCC GGG CGG CGC CGG
Lys Ala Ser Glu Val His Val Arg Ser Ala Arg Ser Ala Pro Gly Arg Arg Arg 279            288             297             306             315             324
CAG CAG GCC CGG AAC CGC TCC ACC CCG GCC CAG GAC GTG TCG CGG GCC TCC AGC
Gln Gln Ala Arg Asn Arg Ser Thr Pro Ala Gln Asp Val Ser Arg Ala Ser Ser 333            342             351             360             369             378
GCC TCA GAC TAC AAC AGC AGC GAG CTG AAG ACG GCC TGC CGG AAG CAT GAG CTC
Ala Ser Asp Tyr Asn Ser Ser Glu Leu Lys Thr Ala Cys Arg Lys His Glu Leu 387            396             405             414             423             432
TAC GTG AGC TTC CAG GAC CTG GGG TGG CAG GAC TGG ATC ATT GCC CCC AAG GGC
Tyr Val Ser Phe Gln Asp Leu Gly Trp Gln Asp Trp Ile Ile Ala Pro Lys Gly 441            450             459             468             477             486
TAC GCT GCC AAC TAC TGT GAC GGA GAA TGT TCG TTC CCT CTC AAC GCA CAC ATG
Tyr Ala Ala Asn Tyr Cys Asp Gly Glu Cys Ser Phe Pro Leu Asn Ala His MET 495            504             513             522             531             540
AAC GCT ACC AAC CAT GCC ATC GTG CAG ACC CTG GTT CAC CTC ATG AAC CCC GAG
Asn Ala Thr Asn His Ala Ile Val Gln Thr Leu Val His Leu MET Asn Pro Glu
```

FIGURE 2
(cont.)

```
     549         558         567         576         585         594
TAC GTC CCC AAA CCG TGC TGC GCG CCC ACG AAA CTG AAC GCC ATC TCG GTG CTC
Tyr Val Pro Lys Pro Cys Cys Ala Pro Thr Lys Leu Asn Ala Ile Ser Val Leu 603         612         621         630         639         648
TAC TTC GAC GAC AAC TCC AAT GTC ATC CTG AAG AAG TAC CGG AAC ATG GTC GTA
Tyr Phe Asp Asp Asn Ser Asn Val Ile Leu Lys Lys Tyr Arg Asn MET Val Val 657         666         676         686         696         706
716

CGA GCG TGT GGG TGC CAC  TGACTCGGGG TGAGTGGCTG GGGACGCTGT GCACACACTG
CCTGGACTCC
Arg Ala Cys Gly Cys His
               (222)
       726        736        746        756        766        776        786
   TGGATCACGT CCGCCTTAAG CCCACAGAGG CCCCCGGGAC ACAGGAGGAG ACCCCGAGGC CACCTTCGGC
       796        806        816        826        836        846        856
   TGGCGTTGGC CTTTCCGCCC AACGCAGACC CGAAGGGACC CTGTCCGCCC CTTGCTCACA CCGTGAGCGT
       866        876        886
   TGTGAGTAGC CATCGGGCTC TAGGAAGCAG CACTCGAG
```

FIGURE 3

```
            9              18              27              36              45              54
CAA CAG AGT CGT AAT CGC TCT ACC CAG TCC CAG GAC GTG GCG CGG GTC TCC AGT
Gln Gln Ser Arg Asn Arg Ser Thr Gln Ser Gln Asp Val Ala Arg Val Ser Ser
(1)
            63             72              81              90              99             108
GCT TCA GAT TAC AAC AGC AGT GAA TTG AAA ACA GCC TGC AGG AAG CAT GAG CTG
Ala Ser Asp Tyr Asn Ser Ser Glu Leu Lys Thr Ala Cys Arg Lys His Glu Leu 117             126             135             144             153             162
TAT GTG AGT TTC CAA GAC CTG GGA TGG CAG GAC TGG ATC ATT GCA CCC AAG GGC
Tyr Val Ser Phe Gln Asp Leu Gly Trp Gln Asp Trp Ile Ile Ala Pro Lys Gly 171             180             189             198             207             216
TAT GCT GCC AAT TAC TGT GAT GGA GAA TGC TCC TTC CCA CTC AAC GCA CAC ATG
Tyr Ala Ala Asn Tyr Cys Asp Gly Glu Cys Ser Phe Pro Leu Asn Ala His MET 225             234             243             252             261             270
AAT GCA ACC AAC CAC GCG ATT GTG CAG ACC TTG GTT CAC CTT ATG AAC CCC GAG
Asn Ala Thr Asn His Ala Ile Val Gln Thr Leu Val His Leu MET Asn Pro Glu 279             288             297             306             315             324
TAT GTC CCC AAA CCG TGC TGT GCG CCA ACT AAG CTA AAT GCC ATC TCG GTT CTT
Tyr Val Pro Lys Pro Cys Cys Ala Pro Thr Lys Leu Asn Ala Ile Ser Val Leu 333             342             351             360             369             378
TAC TTT GAT GAC AAC TCC AAT GTC ATT CTG AAA AAA TAC AGG AAT ATG GTT GTA
Tyr Phe Asp Asp Asn Ser Asn Val Ile Leu Lys Lys Tyr Arg Asn MET Val Val 387             396
AGA GCT TGT GGA TGC CAC TAA
Arg Ala Cys Gly Cys His
```

FIGURE 4

```
            10         20         30         40         50
       GTGACCGAGC GGCGCGGACG GCCGCCTGCC CCCTCTGCCA CCTGGGGCGG 60         70         80         90         99
       TGCGGGCCCG GAGCCCGGAG CCCGGGTAGC GCGTAGAGCC GGCGCG ATG
                                                          MET
                                                          (1)

108        117        126        135        144
       CAC GTG CGC TCA CTG CGA GCT GCG GCG CCG CAC AGC TTC GTG GCG
       His Val Arg Ser Leu Arg Ala Ala Ala Pro His Ser Phe Val Ala 153        162        171        180        189
       CTC TGG GCA CCC CTG TTC CTG CTG CGC TCC GCC CTG GCC GAC TTC
       Leu Trp Ala Pro Leu Phe Leu Leu Arg Ser Ala Leu Ala Asp Phe 198        207        216        225        234
       AGC CTG GAC AAC GAG GTG CAC TCG AGC TTC ATC CAC CGG CGC CTC
       Ser Leu Asp Asn Glu Val His Ser Ser Phe Ile His Arg Arg Leu 243        252        261        270        279
       CGC AGC CAG GAG CGG CGG GAG ATG CAG CGC GAG ATC CTC TCC ATT
       Arg Ser Gln Glu Arg Arg Glu MET Gln Arg Glu Ile Leu Ser Ile 288        297        306        315        324
       TTG GGC TTG CCC CAC CGC CCG CGC CCG CAC CTC CAG GGC AAG CAC
       Leu Gly Leu Pro His Arg Pro Arg Pro His Leu Gln Gly Lys His 333        342        351        360        369
       AAC TCG GCA CCC ATG TTC ATG CTG GAC CTG TAC AAC GCC ATG GCG
       Asn Ser Ala Pro MET Phe MET Leu Asp Leu Tyr Asn Ala MET Ala 378        387        396        405        414
       GTG GAG GAG GGC GGC GGG CCC GGC GGC CAG GGC TTC TCC TAC CCC
       Val Glu Glu Gly Gly Gly Pro Gly Gly Gln Gly Phe Ser Tyr Pro 423        432        441        450        459
       TAC AAG GCC GTC TTC AGT ACC CAG GGC CCC CCT CTG GCC AGC CTG
       Tyr Lys Ala Val Phe Ser Thr Gln Gly Pro Pro Leu Ala Ser Leu 468        477        486        495        504
       CAA GAT AGC CAT TTC CTC ACC GAC GCC GAC ATG GTC ATG AGC TTC
       Gln Asp Ser His Phe Leu Thr Asp Ala Asp MET Val MET Ser Phe 513        522        531        540        549
       GTC AAC CTC GTG GAA CAT GAC AAG GAA TTC TTC CAC CCA CGC TAC
       Val Asn Leu Val Glu His Asp Lys Glu Phe Phe His Pro Arg Tyr
```

FIGURE 4
(Con't)

```
        558             567             576             585             594
CAC CAT CGA GAG TTC CGG TTT GAT CTT TCC AAG ATC CCA GAA GGG
His His Arg Glu Phe Arg Phe Asp Leu Ser Lys Ile Pro Glu Gly 603             612             621             630             639
GAA GCT GTC ACG GCA GCC GAA TTC CGG ATC TAC AAG GAC TAC ATC
Glu Ala Val Thr Ala Ala Glu Phe Arg Ile Tyr Lys Asp Tyr Ile 648             657             666             675             684
CGG GAA CGC TTC GAC AAT GAG ACG TTC CGG ATC AGC GTT TAT CAG
Arg Glu Arg Phe Asp Asn Glu Thr Phe Arg Ile Ser Val Tyr Gln 693             702             711             720             729
GTG CTC CAG GAG CAC TTG GGC AGG GAA TCG GAT CTC TTC CTG CTC
Val Leu Gln Glu His Leu Gly Arg Glu Ser Asp Leu Phe Leu Leu 738             747             756             765             774
GAC AGC CGT ACC CTC TGG GCC TCG GAG GAG GGC TGG CTG GTG TTT
Asp Ser Arg Thr Leu Trp Ala Ser Glu Glu Gly Trp Leu Val Phe 783             792             801             810             819
GAC ATC ACA GCC ACC AGC AAC CAC TGG GTG GTC AAT CCG CGG CAC
Asp Ile Thr Ala Thr Ser Asn His Trp Val Val Asn Pro Arg His 828             837             846             855             864
AAC CTG GGC CTG CAG CTC TCG GTG GAG ACG CTG GAT GGG CAG AGC
Asn Leu Gly Leu Gln Leu Ser Val Glu Thr Leu Asp Gly Gln Ser 873             882             891             900             909
ATC AAC CCC AAG TTG GCG GGC CTG ATT GGG CGG CAC GGG CCC CAG
Ile Asn Pro Lys Leu Ala Gly Leu Ile Gly Arg His Gly Pro Gln 918             927             936             945             954
AAC AAG CAG CCC TTC ATG GTG GCT TTC TTC AAG GCC ACG GAG GTC
Asn Lys Gln Pro Phe MET Val Ala Phe Phe Lys Ala Thr Glu Val 963             972             981             990             999
CAC TTC CGC AGC ATC CGG TCC ACG GGG AGC AAA CAG CGC AGC CAG
His Phe Arg Ser Ile Arg Ser Thr Gly Ser Lys Gln Arg Ser Gln
                                                            (300)

1008            1017            1026            1035            1044
AAC CGC TCC AAG ACG CCC AAG AAC CAG GAA GCC CTG CGG ATG GCC
Asn Arg Ser Lys Thr Pro Lys Asn Gln Glu Ala Leu Arg MET Ala 1053            1062            1071            1080            1089
AAC GTG GCA GAG AAC AGC AGC AGC GAC CAG AGG CAG GCC TGT AAG
Asn Val Ala Glu Asn Ser Ser Ser Asp Gln Arg Gln Ala Cys Lys
```

FIGURE 4
(Con't)

```
            1098        1107        1116        1125        1134
AAG CAC GAG CTG TAT GTC AGC TTC CGA GAC CTG GGC TGG CAG GAC
Lys His Glu Leu Tyr Val Ser Phe Arg Asp Leu Gly Trp Gln Asp 1143        1152        1161        1170        1179
TGG ATC ATC GCG CCT GAA GGC TAC GCC GCC TAC TAC TGT GAG GGG
Trp Ile Ile Ala Pro Glu Gly Tyr Ala Ala Tyr Tyr Cys Glu Gly 1188        1197        1206        1215        1224
GAG TGT GCC TTC CCT CTG AAC TCC TAC ATG AAC GCC ACC AAC CAC
Glu Cys Ala Phe Pro Leu Asn Ser Tyr MET Asn Ala Thr Asn His 1233        1242        1251        1260        1269
GCC ATC GTG CAG ACG CTG GTC CAC TTC ATC AAC CCG GAA ACG GTG
Ala Ile Val Gln Thr Leu Val His Phe Ile Asn Pro Ile Ser Val 1278        1287        1296        1305        1314
CCC AAG CCC TGC TGT GCG CCC ACG CAG CTC AAT GCC ATC TCC GTC
Pro Lys Pro Cys Cys Ala Pro Thr Gln Leu Asn Ala Ile Ser Val 1323        1332        1341        1350        1359
CTC TAC TTC GAT GAC AGC TCC AAC GTC ATC CTG AAG AAA TAC AGA
Leu Tyr Phe Asp Asp Ser Ser Asn Val Ile Leu Lys Lys Tyr Arg 1368        1377        1386        1399
AAC ATG GTG GTC CGG GCC TGT GGC TGC CAC TAGCTCCTCC
Asn MET Val Val Arg Ala Cys Gly Cys His
                                    (431)

1409       1419       1429       1439       1448
GAGAATTCAG ACCCTTTGGG GCCAAGTTTT TCTGGATCCT CCATTGCTC
```

DNA SEQUENCES ENCODING BMP-7 PROTEINS

CROSS REFERENCE TO RELATED APPLICATIONS

This application is a continuation-in-part of U.S. Ser. No. 370,549 filed Jun. 23, 1989, abandoned, which is a continuation-in-part of U.S. Ser. No. 347,559 filed May 4, 1989, abandoned, and of U.S. Ser. No. 329,610 filed Mar. 28, 1989, abandoned, which is a continuation-in-part of U.S. Ser. Nos. 179,100, now U.S. Pat. No. 5,013,649; 179,101; and 179,197 filed Apr. 8, 1988, which are continuations-in-part of U.S. Ser. Nos. 028,285 filed Mar. 20, 1987, now abandoned and 031,346 filed Mar. 26, 1987, now U.S. Pat. No. 4,877,864 which are continuations-in-part of U.S. Ser. No. 943,864 filed Dec. 17, 1986, now abandoned and 880,776 filed Jul. 1, 1986, now abandoned.

The present invention relates to a family of purified proteins, termed BMP-7 proteins (wherein BMP is bone morphogenic protein), which may exhibit the ability to induce cartilage and/or bone formation and processes for obtaining them. These proteins may be used to induce bone and/or cartilage formation and in wound healing and tissue repair.

The invention provides human BMP-7 proteins, substantially free from other proteins with which they are co-produced comprising the amino acid sequence set forth in Table IV from amino acid #300 to amino acid #431. This amino acid sequence #300 to #431 is encoded by the DNA sequence of Table IV from nucleotide #994 to #1389. These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein electrophoreses with a molecular weight of approximately 14,000–20,000 daltons. It is contemplated that these proteins are capable of stimulating, promoting, or otherwise inducing cartilage and/or bone formation.

Human BMP-7 proteins of the invention may be produced by culturing a cell transformed with a DNA sequence containing the nucleotide sequence the same or substantially the same as the nucleotide sequence shown in Table IV comprising nucleotide #97 to nucleotide #1389, recovering and purifying from the culture medium a protein comprising the amino acid sequence the same or substantially the same as shown in Table IV from amino acid #300 to amino acid #431.

The invention further provides a method wherein the proteins described above are utilized for obtaining related human protein/s or other mammalian cartilage and/or bone growth protein/s. Such methods are known to those skilled in the art of genetic engineering. One method for obtaining such proteins involves utilizing the human BMP-7 coding sequence or portions thereof from nucleotide #97 to #1389 as a probe for screening genomic and/or cDNA libraries to isolate the genomic and/or cDNA sequence. These proteins are produced by culturing a cell transformed with the DNA identified as in the method described above which DNA hybridizes under stringent conditions to the nucleotide sequence substantially as shown in Table IV from nucleotide #97 to nucleotide #1389 which encodes a protein exhibiting cartilage and/or bone formation activity and recovering and purifying from the culture medium a protein substantially free from other proteinaceous with which it is co-produced, as well as from other contaminants.

The proteins of the invention may be characterized by the ability to promote, stimulate or otherwise induce the formation of cartilage and/or bone formation. It is further contemplated that the ability of these proteins to induce the formation of cartilage and/or bone may be exhibited by the ability to demonstrate cartilage and/or bone formation activity in the rat bone formation assay described below. It is further contemplated that the proteins of the invention demonstrate activity in this rat bone formation assay at a concentration of 10 $\mu$–500 $\mu$g/gram of bone. More particularly, it is contemplated these proteins may be characterized by the ability of 1 $\mu$g of the protein to score at least +2 in the rat bone formation assay described below using either the original or modified scoring method.

Another aspect of the invention provides pharmaceutical compositions containing a therapeutically effective amount of a BMP-7 protein of the invention in a pharmaceutically acceptable vehicle or carrier. The compositions of the invention may be used to induce bone and/or cartilage formation. These compositions may also be used for wound healing and tissue repair. Further compositions of the invention may include in addition to a BMP-7 protein of the present invention at least one other therapeutically useful agent such as the proteins designated BMP-1, BMP-2A and -2B, BMP-3, BMP-5, and BMP-6 disclosed respectively in co-owned U.S. patent applications Ser. No. 179,101, Ser. No. 179,100, and Ser. No. 179,197, Atty Dkt No. 5151B, filed Nov. 15, 1989, and Ser. No. 347,544. Other therapeutically useful agents include growth factors such as epidermal growth factor (EGF), fibroblast growth factor (FGF), transforming growth factors (TGF-$\alpha$ and TGF-$\beta$), and platelet derived growth factor (PDGF). The compositions of the invention may also include an appropriate matrix, for instance, for supporting the composition and/or providing a surface for bone and/or cartilage formation.

The compositions may be employed in methods for treating a number of bone and/or cartilage defects, and periodontal disease. They may also be employed in methods for treating various types of wounds and in tissue repair. These methods, according to the invention, entail administering to a patient needing such bone and/or cartilage formation, wound healing or tissue repair, a therapeutically effective amount of a protein of the invention. These methods may also entail the administration of a protein of the invention in conjunction with at least one of the "BMP" proteins disclosed in the co-owned applications described above. In addition, these methods may also include the administration of a protein of the invention with other growth factors including EGF, FGF, TGF-$\alpha$, TGF-$\beta$, and PDGF.

Still a further aspect of the invention are DNA sequences coding for expression of a protein of the invention. Such sequences include the sequence of nucleotides in a 5' to 3' direction illustrated in Table IV or DNA sequences which hybridize under stringent conditions with the DNA sequence of Table IV and encode a protein demonstrating ability to induce cartilage and/or bone formation as in the rat bone formation assay described below. It is contemplated that these proteins may demonstrate activity in this assay at a concentration of 10 $\mu$g–500 $\mu$g/gram of bone. More particularly, it is contemplated that these proteins demonstrate the ability of 1 μg of the protein to score at least +2 in the rat bone formation assay. Finally, allelic or other variations of the sequences of Table IV whether such nucleotide changes result in changes in the peptide sequence or not, are also included in the present invention.

A further aspect of the invention provides a vector containing a DNA sequence as described above in operative association with an expression control sequence therefor. These vectors may be employed in a novel process for producing a protein of the invention in which a cell line transformed with a DNA sequence directing expression of a protein of the invention in operative association with an expression control sequence therefor, is cultured in a suitable culture medium and a protein of the invention is recovered and purified therefrom. This claimed process may employ a number of known cells, both prokaryotic and eukaryotic, as host cells for expression of the polypeptide.

Other aspects and advantages of the present invention will be apparent upon consideration of the following detailed description and preferred embodiments thereof.

BRIEF DESCRIPTION OF THE DRAWING

FIG. 1 comprises DNA sequence and derived amino acid sequence of bovine BMP-5. FIG. 1 corresponds to Table I further described below.

FIG. 2 comprises DNA sequence and derived amino acid sequence of bovine BMP-6. FIG. 2 corresponds to Table II further described below.

FIG. 3 comprises DNA sequence and derived amino acid sequence of human BMP-6 from lambda U2-7 ATCC #68021. FIG. 3 corresponds to Table III further described below.

FIG. 4 comprises DNA and amino acid sequence of PEH7-9 ATCC #68182 encoding BMP-7. FIG. 4 corresponds to Table IV further described below.

DETAILED DESCRIPTION OF THE INVENTION

The purified human BMP-7 proteins are characterized by comprising an amino acid sequence as shown in Table IV from amino acid #300-#431. These purified BMP-7 human cartilage/bone proteins of the present invention are produced by culturing a host cell transformed with DNA comprising the DNA sequence as shown in Table IV from nucleotide #97 to nucleotide #1389 or substantially homologous sequences operatively linked to a heterologous regulatory control sequence and recovering, and purifying from the culture medium a protein comprising the amino acid sequence as shown in Table IV from amino acid #300 to amino acid #431 or a substantially homologous sequence. Purified BMP-7 proteins may be produced by culturing a host cell transformed with a DNA comprising the DNA sequence as shown in Table IV from nucleotide #994 - #1389 or substantially homologous sequences operatively linked to a heterologous regulatory control sequence and recovering, and purifying from the culture medium a protein comprising the amino acid sequence as shown in Table IV from amino acid #300 to amino acid #431 or a substantially homologous sequence. The purified human BMP-7 proteins are substantially free from other proteinaceous materials from which they are co-produced, as well as from other contaminants.

These proteins may be further characterized by the ability to demonstrate cartilage and/or bone formation activity. This activity may be demonstrated, for example, in the rat bone formation assay as described in Example III. It is further contemplated that these proteins demonstrate activity in the assay at a concentration of 10 μg-500 lg/gram of bone formed. The proteins may be further characterized by the ability of 1 μg to score at least +2 in this assay using either the original or modified scoring method. BMP-7 proteins may be further characterized by an apparent molecular weight of 28,000-30,000 daltons as determined by sodium dodecyl sulfate polyacrylamide gel electrophoresis (SDS-PAGE). Under reducing conditions in SDS-PAGE the protein electrophoresis with a molecular weight of approximately 14,000-20,000 daltons.

The proteins provided herein also include factors encoded by the sequences similar to those of Table IV but into which modifications are naturally provided (e.g. allelic variations in the nucleotide sequence which may result in amino acid changes in the polypeptide) or deliberately engineered. Similarly, synthetic polypeptides which wholly or partially duplicate continuous sequences of the amino acid residues of Table IV are encompassed by the invention. These sequences, by virtue of sharing primary, secondary, or tertiary structural and conformational characteristics with other cartilage/bone proteins of the invention may possess bone and/or cartilage growth factor biological properties in common therewith. Thus, they may be employed as biologically active substitutes for naturally-occurring proteins in therapeutic processes.

Other specific mutations of the sequences of the proteins of the invention described herein involve modifications of a glycosylation site. These modification may involve O-linked or N-linked glycosylation sites. For instance, the absence of glycosylation or only partial glycosylation results from amino acid substitution or deletion at the asparagine-linked glycosylation recognition sites present in the sequences of the proteins of the invention, for example, as shown in Table IV. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Expression of such altered nucleotide sequences produces variants which are not glycosylated at that site.

The present invention also encompasses the novel DNA sequences, free of association with DNA sequences encoding other proteinaceous materials, and coding on expression for the proteins of the invention. These DNA sequences include those depicted in Tables IV in a 5' to 3' direction. Further included are those sequences which hybridize under stringent hybridization conditions [see, T. Maniatis et al, *Molecular Cloning (A Laboratory Manual)*, Cold Spring Harbor Laboratory (1982), pages 387 to 389] to the DNA sequence of Table IV and demonstrate cartilage and/or bone formation activity in the rat bone formation assay. An example of one such stringent hybridization condition is hybridization at 4×SSC at 65° C., followed by a washing in 0.1×SCC at 65° C. for an hour. Alternatively, an exemplary stringent hybridization condition is in 50% formamide, 4×SCC at 42° C.

Similarly, DNA sequences which encode proteins similar to the protein encoded by the sequence of Table IV, but which differ in codon sequence due to the degeneracies of the genetic code or allelic variations (naturally-occurring base changes in the species population which may or may not result in an amino acid change) also encode the proteins of the invention described herein. Variations in the DNA sequences of Table IV which are caused by point mutations or by induced modifications (including insertion, deletion, and substitution) to enhance the activity, half-life or production of the polypeptides encoded thereby are also encompassed in the invention.

In a further aspect, the invention provides a method for obtaining related human proteins or other mammalian BMP-7 proteins. One method for obtaining such proteins entails, for instance, utilizing the human BMP-7 coding sequence disclosed herein to probe a human genomic library using standard techniques for the human gene or fragments thereof. Sequences thus identified may also be used as probes to identify a human cell line or tissue which synthesizes the analogous cartilage/bone protein. A cDNA library is synthesized and screened with probes derived from the human or bovine coding sequences. The human sequence thus identified is transformed into a host cell, the host cell is cultured and the protein recovered, isolated and purified from the culture medium. The purified protein is predicted to exhibit cartilage and/or bone formation activity in the rat bone formation assay of Example III.

Another aspect of the present invention provides a novel method for producing the proteins of the invention. The method of the present invention involves culturing a suitable cell line, which has been transformed with a DNA sequence coding for expression of a protein of the invention, under the control of known regulatory sequences. Methods for culturing suitable cell lines are within the skill of the art. The transformed cells are cultured and the BMP-7 proteins expressed thereby are recovered and purified from the culture medium using purification techniques known to those skilled in the art.

Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Other suitable mammalian cell lines are the monkey COS-1 cell line and the CV-1 cell line.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of the proteins of the invention. Preferably the vectors contain the full novel DNA sequences described above which code for the novel BMP-6 proteins of the invention. Additionally the vectors also contain appropriate expression control sequences permitting expression of the protein sequences. Alternatively, vectors incorporating modified sequences as described above are also embodiments of the present invention and useful in the production of the proteins of the invention. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to those skilled in the art and may be selected depending upon the selected host cells. Such selection is routine and does not form part of the present invention. Host cells transformed with such vectors and progeny thereof for use in producing BMP-7 proteins are also provided by the invention.

A protein of the present invention, which induces cartilage and/or bone formation in circumstances where bone and/or cartilage is not normally formed, has application in the healing of bone fractures and cartilage defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A protein of the invention may be used in the treatment of periodontal disease, and in other tooth repair processes. Such agents may provide an environment to attract bone-forming cells, stimulate growth of bone-forming cells or induce differentiation of progenitors of bone-forming cells. A variety of osteogenic, cartilage-inducing and bone inducing factors have been described. See, e.g. European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair).

A further aspect of the invention is a therapeutic method and composition for repairing fractures and other conditions related to bone and/or cartilage defects or periodontal diseases. In addition, the invention comprises therapeutic methods and compositions for wound healing and tissue repair. Such compositions comprise a therapeutically effective amount of at least one of the BMP-7 proteins of the invention in admixture with a pharmaceutically acceptable vehicle, carrier or matrix. It is expected that the proteins of the invention may act in concert with or perhaps synergistically with one another or with other related proteins and growth factors. Therapeutic methods and compositions of the invention therefore comprise one or more of the proteins of the present invention. Further therapeutic methods and compositions of the invention therefore comprise a therapeutic amount of at least one protein of the invention with a therapeutic amount of at least one of the other "BMP" proteins disclosed in co-owned and co-pending U.S. applications described above. Such methods and compositions of the invention may comprise proteins of the invention or portions thereof in combination with the above-mentioned "BMP" proteins or portions thereof. Such combination may comprise individual molecules from each of the proteins or heteromolecules such as heterodimers formed by portions of the respective proteins. For example, a method and composition of the invention may comprise a protein of the invention or a portion thereof linked with a portion of a "BMP" protein to form a heteromolecule.

Further therapeutic methods and compositions of the invention comprise the proteins of the invention or portions thereof in combination with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), transforming growth factors (TGF-α and TGF-β), and insulin-like growth factor (IGF-I and IGF-II). Portions of these agents may also be used in compositions of the invention.

The preparation and formulation of such physiologically acceptable protein compositions, having due regard to pH, isotonicity, stability and the like, is within the skill of the art. The therapeutic compositions are also presently valuable for veterinary applications due to the apparent lack of species specificity in cartilage and bone growth factor proteins. Domestic animals and thoroughbred horses in addition to humans are desired patients for such treatment with the proteins of the present invention.

The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of cartilage and/or bone or tissue damage. Topical administration may be suitable for wound healing and tissue repair. Preferably for bone and/or cartilage formation, the composition would include a matrix capable of delivering the BMP-7 proteins of the invention to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions of the invention will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the proteins of the invention. Factors which may modify the action of the proteins of the invention include the amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the type or types of bone and/or cartilage proteins present in the composition. The addition of other known growth factors, such as EGF, PDGF, TGF-α, TGF-β, and IGF-I and IGF-II to the final composition, may also effect the dosage.

Progress can be monitored by periodic assessment of cartilage and/or bone growth and/or repair. The progress can be monitored, for example, using x-rays, histomorphometric determinations and tetracycline labeling.

The following examples illustrate practice of the present invention in recovering and characterizing bovine cartilage and/or bone proteins of the invention and employing these proteins to recover the corresponding human protein or proteins and in expressing the proteins via recombinant techniques.

EXAMPLE I

Isolation of Bovine Cartilaqe/Bone Inductive Protein

Ground bovine bone powder (20-120 mesh, Helitrex) is prepared according to the procedures of M. R. Urist et al., *Proc. Natl Acad. Sci USA*, 70:3511 (1973) with elimination of some extraction steps as identified below. Ten kgs of the ground powder is demineralized in successive changes of 0.6N HCl at 40° C. over a 48 hour period with vigorous stirring. The resulting suspension is extracted for 16 hours at 40° C. with 50 liters of 2M $CaCl_2$ and 10 mM ethylenediamine-tetraacetic acid [EDTA], and followed by extraction for 4 hours in 50 liters of 0.5M EDTA. The residue is washed three times with distilled water before its resuspension in 20 liters of 4M guanidine hydrochloride [GuCl], 20 mM Tris (pH 7.4), 1 mM N-ethylmaleimide, lmM iodoacetamide, 1 mM phenylmethylsulfonyl fluorine as described in *Clin. Orthop. Rel. Res.*, 171: 213 (1982). After 16 to 20 hours the supernatant is removed and replaced with another 10 liters of GuCl buffer. The residue is extracted for another 24 hours.

The crude GuCl extracts are combined, concentrated approximately 20 times on a Pellicon apparatus with a 10,000 molecular weight cut-off membrane, and then dialyzed in 50 mM Tris, 0.1M NaCl, 6M urea (pH7.2), the starting buffer for the first column. After extensive dialysis the protein is loaded on a 4 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath - Reddi assay (described in Example III below) desorbed from the column by 50 mM NaAc, 0.25 mM NaCl, 6M urea (pH 4.6). The protein from this step elution is concentrated 20- to 40-fold, then diluted 5 times with 80 mM $KPO_4$, 6M urea (pH6.0). The pH of the solution is adjusted to 6.0 with 500 mM $K_2HPO_4$. The sample is applied to an hydroxylapatite column (LKB) equilibrated in 80 mM $KPO_4$, 6M urea (pH6.0) and all unbound protein is removed by washing the column with the same buffer. Protein having bone and-/or cartilage formation activity is eluted with 100 mM $KPO_4$ (pH7.4) and 6M urea.

The protein is concentrated approximately 10 times, and solid NaCl added to a final concentration of 0.15M. This material is applied to a heparin - Sepharose column equilibrated in 50 mM $KPO_4$, 150 mM NaCl, 6M urea (pH7.4). After extensive washing of the column with starting buffer, a protein with bone and/or cartilage inductive activity is eluted by 50 mM $KPO_4$, 700 mM NaCl, 6M urea (pH7.4). This fraction is concentrated to a minimum volume, and 0.4 ml aliquots are applied to Superose 6 and Superose 12 columns connected in series, equilibrated with 4M GuCl, 20 mM Tris (pH7.2) and the columns developed at a flow rate of 0.25 ml/min. The protein demonstrating bone and/or cartilage inductive activity corresponds to an approximate 30,000 dalton protein.

The above fractions from the superose columns are pooled, dialyzed against 50 mM NaAc, 6M urea (pH4.6), and applied to a Pharmacia MonoS HR column. The column is developed with a gradient to 1.0M NaCl, 50 mM NaAc, 6M urea (pH4.6). Active bone and/or cartilage formation fractions are pooled. The material is applied to a 0.46×25 cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1 ml per minute). Active material is eluted at approximately 40–44% acetonitrile. Fractions were assayed for cartilage and/or bone formation activity. The active material is further fractionated on a MonoQ column. The protein is dialyzed against 6M urea, 25 mM diethanolamine, pH 8.6 and then applied to a 0.5 by 5 cm MonoQ column (Pharmacia) which is developed with a gradient of 6M urea, 25 mM diethanolamine, pH 8.6 and 0.5 M NaCl, 6M urea, 25 mM diethanolamine, pH 8.6. Fractions are brought to pH3.0 with 10% trifluoroacetic acid (TFA).

Aliquots of the appropriate fractions are iodinated by one of the following methods: P. J. McConahey et al, *Int. Arch. Allergy*, 29:185–189 (1966); A. E. Bolton et al, *Biochem J.*, 133:529 (1973); and D. F. Bowen-Pope, *J. Biol. Chem.*, 237:5161 (1982). The iodinated proteins present in these fractions are analyzed by SDS gel electrophoresis.

EXAMPLE II

Characterization of Bovine Cartilage/Bone Inductive Factor

A. Molecular Weight

Approximately 5 μg protein from Example I in 6M urea, 25 mM diethanolamine, pH 8.6, approximately 0.3 M NaCl is made 0.1% with respect to SDS and dialyzed against 50 mM tris/HCl 0.1% SDS pH 7.5 for 16 hrs. The dialyzed material is then electrophorectically concentrated against a dialysis membrane [Hunkapillar et al *Meth. Enzymol.* 91: 227–236 (1983)] with a small amount of I 125 labelled counterpart. This material (volume approximately 100 μl) is loaded onto a 12% polyacrylamide gel and subjected to SDS-PAGE [Laemmli, U.K. *Nature*, 227:680–685 (1970)]without reducing the sample with dithiothreitol. The molecular weight is determined relative to prestained molecular weight standards (Bethesda Research Labs). Following autoradiography of the unfixed gel the approximate 28,000–30,000 dalton band is excised and the protein electrophoretically eluted from the gel (Hunkapillar et al supra). Based on similar purified bone fractions as described in the co-pending "BMP" applications described above wherein bone and/or cartilage activity is found in the 28,000–30,000 region, it is inferred that this band comprises bone and/or cartilage inductive fractions.

B. Subunit Characterization

The subunit composition of the isolated bovine bone protein is also determined. The eluted protein described above is fully reduced and alkylated in 2% SDS using iodoacetate and standard procedures and reconcentrated by electrophoretic packing. The fully reduced and alkylated sample is then further submitted to SDS-PAGE on a 12% gel and the resulting approximate 14,000–20,000 dalton region having a doublet appearance located by autoradiography of the unfixed gel. A faint band remains at the 28,000–30,000 region. Thus the 28,000–30,000 dalton protein yields a broad region of 14,000–20,000 which may otherwise also be interpreted and described as comprising two broad bands of approximately 14,000–16,000 and 16,000–18,000 daltons.

EXAMPLE III

Rosen Modified Sampath-Reddi Assay

A modified version of the rat bone formation assay described in Sampath and Reddi, *Proc. Natl. Acad. Sci. U.S.A.*, 80:6591 ∝ 6595 (1983) is used to evaluate bone and/or cartilage activity of the proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [See, A. H. Reddi et al., *Proc. Natl Acad Sci.*, 69:1601 (1972)].

The other half of each implant is fixed and processed for histological analysis. Glycolmethacrylate sections (1 μm) are stained with Von Kossa and acid fuschin or toluidine blue to score the amount of induced bone and cartilage formation present in each implant. The terms +1 through +5 represent the area of each histological section of an implant occupied by new bone and/or cartilage cells and newly formed bone and matrix. Two scoring methods are herein described. The first describes the original scoring method while the second describes the later adopted scoring method. A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone. The scoring method later adopted (which hereinafter may be referred to as the modified scoring method) is as follows: three non-adjacent sections are evaluated from each implant and averaged. "±" indicates tentative identification of cartilage or bone; "+1" indicates >10% of each section being new cartilage or bone; "+2", >25%; "+3", 50%; "+4", ~75%; "+5", >80%. The scores of the individual implants are tabulated to indicate assay variability.

It is contemplated that the dose response nature of the cartilage and/or bone inductive protein containing samples of the matrix samples will demonstrate that the amount of bone and/or cartilage formed increases with the amount of cartilage/bone inductive protein in the sample. It is contemplated that the control samples will not result in any bone and/or cartilage formation.

As with other cartilage and/or bone inductive proteins such as the above-mentioned "BMP" proteins, the bone and/or cartilage formed is expected to be physically confined to the space occupied by the matrix. Samples are also analyzed by SDS gel electrophoresis and isoelectric focusing followed by autoradiography. The activity is correlated with the protein bands and pI. To estimate the purity of the protein in a particular fraction an extinction coefficient of 1 OD/mg-cm is used as an estimate for protein and the protein is run on SDS-PAGE followed by silver staining or radioiodination and autoradiography.

EXAMPLE IV

Bovine Protein Composition

The gel slice of the approximate 14,000–20,000 dalton region described in Example IIB is fixed with methanol-acetic acid-water using standard procedures, briefly rinsed with water, then neutralized with 0.1M ammonium bicarbonate. Following dicing the gel slice with a razor blade, the protein is digested from the gel matrix by adding 0.2 μg of TPCK-treated trypsin (Worthington) and incubating the gel for 16 hr. at 37 degrees centigrade. The resultant digest is then subjected to RPHPLC using a C4 Vydac RPHPLC column and 0.1% TFA-water 0.1% TFA water-acetonitrile gradient. The resultant peptide peaks were monitored by UV absorbance at 214 and 280 nm and subjected to direct amino terminal amino acid sequence analysis using an Applied Biosystems gas phase sequenator (Model 470A). One tryptic fragment is isolated by standard procedures having the following amino acid sequence as represented by the amino acid standard three-letter symbols and where "Xaa" indicates an unknown amino acid the amino acid in parentheses indicates uncertainty in the sequence:

Xaa-His-Glu-Leu-Tyr-Val-Ser-Phe-(Ser)

The following four oligonucleotide probes are designed on the basis of the amino acid sequence of the above-identified tryptic fragment and synthesized on an automated DNA synthesizer.
PROBE #1: GTRCTYGANATRCANTC
PROBE #2: GTRCTYGANATRCANAG
PROBE #3: GTRCTYAAYATRCANTC
PROBE #4: GTRCTYAAYATRCANAG The standard nucleotide symbols in the above identified probes are as follows: A,adenosine; C,cytosine; G,guanine; T,thymine; N, adenosine or cytosine or guanine or thymine; R,adenosine or guanine; and Y,-cytosine or thymine.

Each of the probes consists of pools of oligonucleotides. Because the genetic code is degenerate (more than one codon can code for the same amino acid), a mixture of oligonucleotides is synthesized that contains all possible nucleotide sequences encoding the amino acid sequence of the tryptic. These probes are radioactively labeled and employed to screen a bovine cDNA library as described below.

Poly(A) containing RNA is isolated by oligo(dT) cellulose chromatography from total RNA isolated from fetal bovine bone cells by the method of Gehron-Robey et al in *Current Advances in Skeletogenesis*, Elsevier Science Publishers (1985). The total RNA was obtained from Dr. Marion Young, National Institute of Dental Research, National Institutes of Health. A cDNA library is made in lambda gt10 (Toole et al supra) and plated on 50 plates at 8000 recombinants per plate. These recombinants (400,000) are screened on duplicate nitrocellulose filters with a combination of Probes 1, 2, 3, and 4 using the Tetramethylammonium chloride (TMAC) hybridization procedure [see Wozney et al *Science*, 242: 1528–1534 (1988)]. Twenty-eight positives are obtained and are replated for secondaries. Duplicate nitrocellulose replicas again are made. One set of filters are screened with Probes 1 and 2; the other with Probes 3 and 4. Six positives are obtained on the former, 21 positives with the latter. One of the six, called HEL5, is plague purified, a phage plate stock made, and bacteriophage DNA isolated. This DNA is digested with EcoRI and subcloned into M13 and pSP65 (Promega Biotec, Madison, Wis.) [Melton, et al. *Nucl. Acids Res.* 12: 7035–7056 (1984)]. The DNA sequence and derived amino acid sequence of this fragment is shown in Table I.

DNA sequence analysis of this fragment in M13 indicates that it encodes the desired tryptic peptide sequence set forth above, and this derived amino acid sequence is preceded by a basic residue (Lys) as predicted by the specificity of trypsin. The underlined portion of the sequence in Table I from amino acid #42 to #48 corresponds to the tryptic fragment identified above from which the oligonucleotide probes are designed. The derived amino acid sequence Ser-Gly-Ser-His-Gln-Asp-Ser-Ser-Arg as set forth in Table I from amino acid #15 to #23 is noted to be similar to a tryptic fragment sequence Ser-Thr-Pro-Ala-Gln-Asp-Val-Ser-Arg found in the 28,000–30,000 dalton purified bone preparation as described in the "BMP" co-pending applications Ser. Nos. 179,101, 179,100, and 179,197 mentioned above. This fragment set forth in Table I is a portion of the DNA sequence which encodes a bovine BMP-5 protein the human homologue of which is further described in copending U.S. patent application Ser. No. 329,610. The DNA sequence shown in Table I indicates an open reading frame from the 5' end of the clone of 420 base pairs, encoding a partial peptide of 140 amino acid residues (the first 7 nucleotides are of the adaptors used in the cloning procedure). An in-frame stop codon (TAA) indicates that this clone encodes the carboxy-terminal part of bovine BMP-5.

TABLE I

1 TCTAGAGGTGAGAGCAGCCAACAAGAGAAAAAATCAAAACCGCAATAAATCCGGCTCTCAT
Leu Glu Val Arg Ala Ala Asn Lys Arg Lys Asn Gln Asn Arg Asn Lys <u>Ser Gly Ser His</u>
(1)                                                                              (15)

TABLE I-continued

```
 62 CAGGACTCCTCTAGAATGTCCAGTGTTGGAGATTATAACACCAGTGAACAAAAACAAGCC
    Gln Asp Ser Ser Arg Met Ser Ser Val Gly Asp Tyr Asn Thr Ser Glu Gln Lys Gln Ala
                    (23)

122 TGTAAAAAGCATGAACTCTATGTGAGTTTCCGGGATCTGGGATGGCAGGACTGGATTATA
    Cys Lys Lys His Glu Leu Tyr Val Ser Phe Arg Asp Leu Gly Trp Gln Asp Trp Ile Ile
                      (42)

182 GCACCAGAAGGATATGCTGCATTTTATTGTGATGGAGAATGTTCTTTTCCACTCAATGCC
    Ala Pro Glu Gly Tyr Ala Ala Phe Tyr Cys Asp Gly Glu Cys Ser Phe Pro Leu Asn Ala

242 CATATGAATGCCACCAATCATGCCATAGTTCAGACTCTGGTTCACCTGATGTTTCCTGAC
    His Met Asn Ala Thr Asn His Ala Ile Val Gln Thr Leu Val His Leu Met Phe Pro Asp

302 CACGTACCAAAGCCTTGCTGCGCGACAAACAAACTAAATGCCATCTCTGTGTTGTACTTT
    His Val Pro Lys Pro Cys Cys Ala Thr Asn Lys Leu Asn Ala Ile Ser Val Leu Tyr Phe

362 GATGACAGCTCCAATGTCATTTTGAAAAAGTACAGAAATATGGTCGTGCGTTCGTGTGGT
    Asp Asp Ser Ser Asn Val Ile Leu Lys Lys Tyr Arg Asn Met Val Val Arg Ser Cys Gly

422 TGCCACTAATAGTGCATAATAATGGTAATAAGAAAAAAGATCTGTATGGAGGTTTATGA
    Cys His End (140)

481 CTACAATAAAAAATATCTTTCGGATAAAAGGGGAATTTAATAAAATTAGTCTGGCTCATT

541 TCATCTCTGTAACCTATGTACAAGAGCATGTATATAGT 578
```

The remaining positive clones isolated with probes #1, #2, #3, and #4 described above are screened with HEL5 and a further clone is identified that hybridizes under reduced hybridization conditions [5x SSC, 0.1% SDS, 5X Denhardt's, 100 μg/ml salmon sperm DNA standard hybridization buffer (SHB) at 65° C., wash in 2XSSC 0.1% SDS at 65° C.]. This clone is plaque purified, a phage plate stock made and bacteriophage DNA isolated. The DNA sequence and derived amino acid sequence of a portion of this clone is shown in Table II. This sequence represents a portion of the DNA sequence encoding a BMP-6 cartilage/bone protein, the human homologue of which is further described in co-pending application Ser. No. 370,544.

The first underlined portion of the sequence in Table II from amino acid #97—amino acid #105 corresponds to the tryptic fragment found in the 28,000-30,000 dalton purified bovine bone preparation (and its reduced form at approximately 18,000-20,000 dalton reduced form) as described in the "BMP" co-pending applications mentioned above. The second underlined sequence in Table II from amino acid #124—amino acid #130 corresponds to the tryptic fragment identified above from which the oligonucleotide probes are designed.

The DNA sequence of Table II indicates an open reading frame of 666 base pairs starting from the 5' end of the sequence of Table II, encoding a partial peptide of 222 amino acid residues. An in-frame stop codon (TGA) indicates that this clone encodes the carboxy-terminal part of a bovine BMP-6 protein. Based on knowledge of other BMP proteins and other proteins in the TGF-β family, it is predicted that the precursor polypeptide would be cleaved at the three basic residues (ArgArgArg) to yield a mature peptide beginning with residue 90 or 91 of the sequence of Table II.

TABLE II

```
            9              18              27              36              45              54
    CTG CTG GGC    ACG CGT GCT    GTG TGG GCC    TCA GAG GCG    GGC TGG CTG    GAG TTT GAC
    Leu Leu Gly    Thr Arg Ala    Val Trp Ala    Ser Glu Ala    Gly Trp Leu    Glu Phe Asp
    (1)

63             72              81              90              99             108
    ATC ACG GCC    ACC AGC AAC    CTG TGG GTC    CTG ACT CCG    CAG CAC AAC    ATG GGG CTG
    Ile Thr Ala    Thr Ser Asn    Leu Trp Val    Leu Thr Pro    Gln His Asn    MET Gly Leu 117            126             135             144             153             162
    CAG CTG AGC    GTG GTC ACG    CGT GAT GGG    CTC AGC ATC    AGC CCT GGG    GCC GCG GGC
    Gln Leu Ser    Val Val Thr    Arg Asp Gly    Leu Ser Ile    Ser Pro Gly    Ala Ala Gly 171            180             189             198             207             216
    CTG GTG GGC    AGG GAC GGC    CCC TAC GAC    AAG CAG CCC    TTC ATG GTG    GCC TTC TTC
    Leu Val Gly    Arg Asp Gly    Pro Tyr Asp    Lys Gln Pro    Phe MET Val    Ala Phe Phe 225            234             243             252             261             270
    AAG GCC AGT    GAG GTC CAC    GTG CGC AGT    GCC CGG TCG    GCC CCC GGG    CGG CGC CGG
    Lys Ala Ser    Glu Val His    Val Arg Ser    Ala Arg Ser    Ala Pro Gly    Arg Arg Arg 279            288             297             306             315             324
    CAG CAG GCC    CGG AAC CGC    TCC ACC CCG    GCC CAG GAC    GTG TCG CGG    GCC TCC AGC
    Gln Gln Ala    Arg Asn Arg    Ser Thr Pro    Ala Gln Asp    Val Ser Arg    Ala Ser Ser
```

TABLE II-continued

```
          333         342         351         360         369         378
       GCC TCA     GAC TAC     AAC AGC     AGC GAG     CTG AAG     ACG GCC     TGC CGG     AAG CAT     GAG CTC
       Ala Ser     Asp Tyr     Asn Ser     Ser Glu     Leu Lys     Thr Ala     Cys Arg     Lys His     Glu Leu 387         396         405         414         423         432
       TAC GTG     AGC TTC     CAG GAC     CTG GGG     TGG CAG     GAC TGG     ATC ATT     GCC CCC     AAG GGC
       Tyr Val     Ser Phe     Gln Asp     Leu Gly     Trp Gln     Asp Trp     Ile Ile     Ala Pro     Lys Gly 441         450         459         468         477         486
       TAC GCT     GCC AAC     TAC TGT     GAC GGA     GAA TGT     TCG TTC     CCT CTC     AAC GCA     CAC ATG
       Tyr Ala     Ala Asn     Tyr Cys     Asp Gly     Glu Cys     Ser Phe     Pro Leu     Asn Ala     His MET 495         504         513         522         531         540
       AAC GCT     ACC AAC     CAT GCC     ATC GTG     CAG ACC     CTG GTT     CAC CTC     ATG AAC     CCC GAG
       Asn Ala     Thr Asn     His Ala     Ile Val     Gln Thr     Leu Val     His Leu     MET Asn     Pro Glu 549         558         567         576         585         594
       TAC GTC     CCC AAA     CCG TGC     TGC GCG     CCC ACG     AAA CTG     AAC GCC     ATC TCG     GTG CTC
       Tyr Val     Pro Lys     Pro Cys     Cys Ala     Pro Thr     Lys Leu     Asn Ala     Ile Ser     Val Leu 603         612         621         630         639         648
       TAC TTC     GAC GAC     AAC TCC     AAT GTC     ATC CTG     AAG AAG     TAC CGG     AAC ATG     GTC GTA
       Tyr Phe     Asp Asp     Asn Ser     Asn Val     Ile Leu     Lys Lys     Tyr Arg     Asn MET     Val Val 657         666         676         686         696         706          716
       CGA GCG     TGT GGG     TGC CAC     TGACTCGGGG   TGAGTGGCTG  GGGACGCTGT  GCACACACTG  CCTGGACTCC
       Arg Ala     Cys Gly     Cys His
                                   (222)

726         736         746         756         766         776         786
             TGGATCACGT  CCGCCTTAAG  CCCACAGAGG  CCCCCGGGAC  ACAGGAGGAG  ACCCCGAGGC  CACCTTCGGC 796         806         816         826         836         846         856
             TGGCGTTGGC  CTTTCCGCCC  AACGCAGACC  CGAAGGGACC  CTGTCCGCCC  CTTGCTCACA  CCGTGAGCGT 866         876         886
             TGTGAGTAGC  CATCGGGCTC  TAGGAAGCAG  CACTCGAG
```

EXAMPLE V

Human Proteins

Human cell lines which synthesize BMP-5 and/or BMP-6 mRNAs are identified in the following manner. RNA is isolated from a variety of human cell lines, selected for poly(A)-containing RNA by chromatography on oligo(dT) cellulose, electrophoresed on a formaldehyde-agarose gel, and transferred to nitrocellulose. A nitrocellulose replica of the gel is hybridized to a single stranded M13 $^{32}$P-labeled probe corresponding to the above mentioned BMP-5 EcoRI-BglII fragment containing nucleotides 1-465 of the sequence of Table I. A strongly hybridizing band is detected in the lane corresponding to the human osteosarcoma cell line U-2OS RNA. Another nitrocellulose replica is hybridized to a single stranded M13 $^{32}$P-labeled probe containing the PstI-SmaI fragment of bovine BMP-6 (corresponding to nucleotides 106-261 of Table II). It is found that several RNA species in the lane corresponding to U-2OS RNA hybridize to this probe.

A cDNA Library is made in the vector lambda ZAP (Stratagene) from U-2OS poly(A)-containing RNA using established techniques (Toole et al.). 750,000 recombinants of this library are plated and duplicate nitrocellulose replicas made. The SmaI fragment of bovine BMP-6 corresponding to nucleotides 259-751 of Table II is labeled by nick-translation and hybridized to both sets of filters in SHB at 65°. One set of filters is washed under stringent conditions (0.2X SSC, 0.1% SDS at 65°), the other under reduced stringency conditions (1X SSC, 0.1% SDS at 65°). Many duplicate hybridizing recombinants (approximately 162) are noted. 24 are picked and replated for secondaries. Three nitrocellulose replicas are made of each plate. One is hybridized to the BMP-6 SmaI probe, one to a nick-translated BMP-6 PstI-SacI fragment (nucleotides 106-378 of Table II), and the third to the nick-translated BMP-5 XbaI fragments (nucleotides 1-76 of Table I). Hybridization and washes are carried out under stringent conditions.

Six clones which hybridize to the second probe more strongly than to the third are picked and transformed into plasmids. Restriction mapping, Southern blot analysis, and DNA sequence analysis of these plasmids indicate that there are two classes of clones. Clones U2-7 and U2-10 contain human BMP-6 coding sequence based on their stronger hybridization to the second probe and closer DNA homology to the bovine BMP-6 sequence of Table II than the other 4 clones. DNA sequence derived from these clones is given in Table III. This sequence encodes a partial polypeptide of 132 amino acids comprising the carboxyterminus of the human BMP-6 protein. A stop codon (TAA) follows the 396 base pairs of coding sequence. U2-7 was deposited with the American Type Culture Collection (ATCC), Rockville, Md. on Jun. 22, 1989 under accession number ATCC 68021.

The other four clones encode a novel polypeptide which we designate as BMP-7. DNA sequence analysis and derived amino acid sequence of one of these clones, PEH7-9, is given in Table IV. PEH7-9 was deposited with the American Type Culture Collection (ATCC), Rockville, Md. on Nov. 17, 1989 under accession number ATCC 68182. Another BMP-7 clone, U2-5 was deposited with the ATCC on Jun. 22, 1989 under accession number ATCC 68020. PEH7-9 contains an insert of 1448 base pairs. This clone, PEH7-9, is expected to contain all of the nucleotide sequence necessary to encode BMP-7 proteins. The cDNA sequence of Table IV contains an open reading frame of 1292 base pairs, encoding a protein of 431 amino acids, preceded by a 5' untranslated region of 96 base pairs with stop codons in all frames, and contains a 3' untranslated region of 60 base pairs following the in frame stop codon TAG.

This protein of 431 amino acids has a molecular weight of 49,000 daltons as predicted by its amino acid sequence and is contemplated to represent the primary translation product. Based on knowledge of other BMP proteins as well as other proteins within the TGF-β family, it is predicted that the precursor polypeptide would be cleaved between amino acid #299 and #300, yielding a 132 amino acid mature peptide.

The underlined sequence of Table IV from amino acid #309-#314 Asn-Gln-Glu-Ala-Leu-Arg is the same sequence as that of tryptic fragment #5 found in the 28,000-30,000 dalton purified bone preparation as described in the "BMP" co-pending applications mentioned above, including U.S. Ser. Nos. 179,101, 179,100 and 179,197.

The underlined sequence of Table IV from amino acid #333-#339 His-Glu-Leu-Tyr-Val-Ser-Phe corresponds to the tryptic fragment identified in the bovine bone preparation described above from which the oligonucleotide probes are designed.

TABLE III

```
              9           18          27          36          45          54
CAA CAG AGT CGT AAT CGC TCT ACC CAG TCC CAG GAC GTG GCG CGG GTC TCC AGT
Gln Gln Ser Arg Asn Arg Ser Thr Gln Ser Gln Asp Val Ala Arg Val Ser Ser
(1)

63          72          81          90          99         108
GCT TCA GAT TAC AAC AGC AGT GAA TTG AAA ACA GCC TGC AGG AAG CAT GAG CTG
Ala Ser Asp Tyr Asn Ser Ser Glu Leu Lys Thr Ala Cys Arg Lys His Glu Leu 117         126         135         144         153         162
TAT GTG AGT TTC CAA GAC CTG GGA TGG CAG GAC TGG ATC ATT GCA CCC AAG GGC
Tyr Val Ser Phe Gln Asp Leu Gly Trp Gln Asp Trp Ile Ile Ala Pro Lys Gly 171         180         189         198         207         216
TAT GCT GCC AAT TAC TGT GAT GGA GAA TGC TCC TTC CCA CTC AAC GCA CAC ATG
Tyr Ala Ala Asn Tyr Cys Asp Gly Glu Cys Ser Phe Pro Leu Asn Ala His MET 225         234         243         252         261         270
AAT GCA ACC AAC CAC GCG ATT GTG CAG ACC TTG GTT CAC CTT ATG AAC CCC GAG
Asn Ala Thr Asn His Ala Ile Val Gln Thr Leu Val His Leu MET Asn Pro Glu 279         288         297         306         315         324
TAT GTC CCC AAA CCG TGC TGT GCG CCA ACT AAG CTA AAT GCC ATC TCG GTT CTT
Tyr Val Pro Lys Pro Cys Cys Ala Pro Thr Lys Leu Asn Ala Ile Ser Val Leu 333         342         351         360         369         378
TAC TTT GAT GAC AAC TCC AAT GTC ATT CTG AAA AAA TAC AGG AAT ATG GTT GTA
Tyr Phe Asp Asp Asn Ser Asn Val Ile Leu Lys Lys Tyr Arg Asn MET Val Val 387         396
AGA GCT TGT GGA TGC CAC TAA
Arg Ala Cys Gly Cys His
```

TABLE IV

```
             10          20          30          40          50
        GTGACCGAGC  GGCGCGGACG  GCCGCCTGCC  CCCTCTGCCA  CCTGGGGCGG 60          70          80          90          99
        TGCGGGCCCG  GAGCCCGGAG  CCCGGGTAGC  GCGTAGAGCC  GGCGCG ATG
                                                              MET
                                                              (1)

108         117         126         135         144
CAC GTG CGC TCA CTG CGA GCT GCG GCG CCG CAC AGC TTC GTG GCG
His Val Arg Ser Leu Arg Ala Ala Ala Pro His Ser Phe Val Ala 153         162         171         180         189
CTC TGG GCA CCC CTG TTC CTG CTG CGC TCC GCC CTG GCC GAC TTC
Leu Trp Ala Pro Leu Phe Leu Leu Arg Ser Ala Leu Ala Asp Phe 198         207         216         225         234
AGC CTG GAC AAC GAG GTG CAC TCG AGC TTC ATC CAC CGG CGC CTC
Ser Leu Asp Asn Glu Val His Ser Ser Phe Ile His Arg Arg Leu 243         252         261         270         279
CGC AGC CAG GAG CGG CGG GAG ATG CAG CGC GAG ATC CTC TCC ATT
Arg Ser Gln Glu Arg Arg Glu MET Gln Arg Glu Ile Leu Ser Ile 288         297         306         315         324
TTG GGC TTG CCC CAC CGC CCG CGC CCG CAC CTC CAG GGC AAG CAC
Leu Gly Leu Pro His Arg Pro Arg Pro His Leu Gln Gly Lys His
```

TABLE IV-continued

|     |     |     |     |     |     |     |     |     |     |     |     |     |
|-----|-----|-----|-----|-----|-----|-----|-----|-----|-----|-----|-----|-----|
|     | 333 |     |     | 342 |     |     | 351 |     |     | 360 |     | 369 |
| AAC | TCG | GCA | CCC | ATG | TTC | ATG | CTG | GAC | CTG | TAC | AAC | GCC | ATG | GCG |
| Asn | Ser | Ala | Pro | MET | Phe | MET | Leu | Asp | Leu | Tyr | Asn | Ala | MET | Ala |

|     | 378 |     |     | 387 |     |     | 396 |     |     | 405 |     | 414 |
| GTG | GAG | GAG | GGC | GGC | GGG | CCC | GGC | GGC | CAG | GGC | TTC | TCC | TAC | CCC |
| Val | Glu | Glu | Gly | Gly | Gly | Pro | Gly | Gly | Gln | Gly | Phe | Ser | Tyr | Pro |

|     | 423 |     |     | 432 |     |     | 441 |     |     | 450 |     | 459 |
| TAC | AAG | GCC | GTC | TTC | AGT | ACC | CAG | GGC | CCC | CCT | CTG | GCC | AGC | CTG |
| Tyr | Lys | Ala | Val | Phe | Ser | Thr | Gln | Gly | Pro | Pro | Leu | Ala | Ser | Leu |

|     | 468 |     |     | 477 |     |     | 486 |     |     | 495 |     | 504 |
| CAA | GAT | AGC | CAT | TTC | CTC | ACC | GAC | GCC | GAC | ATG | GTC | ATG | AGC | TTC |
| Gln | Asp | Ser | His | Phe | Leu | Thr | Asp | Ala | Asp | MET | Val | MET | Ser | Phe |

|     | 513 |     |     | 522 |     |     | 531 |     |     | 540 |     | 549 |
| GTC | AAC | CTC | GTG | GAA | CAT | GAC | AAG | GAA | TTC | TTC | CAC | CCA | CGC | TAC |
| Val | Asn | Leu | Val | Glu | His | Asp | Lys | Glu | Phe | Phe | His | Pro | Arg | Tyr |

|     | 558 |     |     | 567 |     |     | 576 |     |     | 585 |     | 594 |
| CAC | CAT | CGA | GAG | TTC | CGG | TTT | GAT | CTT | TCC | AAG | ATC | CCA | GAA | GGG |
| His | His | Arg | Glu | Phe | Arg | Phe | Asp | Leu | Ser | Lys | Ile | Pro | Glu | Gly |

|     | 603 |     |     | 612 |     |     | 621 |     |     | 630 |     | 639 |
| GAA | GCT | GTC | ACG | GCA | GCC | GAA | TTC | CGG | ATC | TAC | AAG | GAC | TAC | ATC |
| Glu | Ala | Val | Thr | Ala | Ala | Glu | Phe | Arg | Ile | Tyr | Lys | Asp | Tyr | Ile |

|     | 648 |     |     | 657 |     |     | 666 |     |     | 675 |     | 684 |
| CGG | GAA | CGC | TTC | GAC | AAT | GAG | ACG | TTC | CGG | ATC | AGC | GTT | TAT | CAG |
| Arg | Glu | Arg | Phe | Asp | Asn | Glu | Thr | Phe | Arg | Ile | Ser | Val | Tyr | Gln |

|     | 693 |     |     | 702 |     |     | 711 |     |     | 720 |     | 729 |
| GTG | CTC | CAG | GAG | CAC | TTG | GGC | AGG | GAA | TCG | GAT | CTC | TTC | CTG | CTC |
| Val | Leu | Gln | Glu | His | Leu | Gly | Arg | Glu | Ser | Asp | Leu | Phe | Leu | Leu |

|     | 738 |     |     | 747 |     |     | 756 |     |     | 765 |     | 774 |
| GAC | AGC | CGT | ACC | CTC | TGG | GCC | TCG | GAG | GAG | GGC | TGG | CTG | GTG | TTT |
| Asp | Ser | Arg | Thr | Leu | Trp | Ala | Ser | Glu | Glu | Gly | Trp | Leu | Val | Phe |

|     | 783 |     |     | 792 |     |     | 801 |     |     | 810 |     | 819 |
| GAC | ATC | ACA | GCC | ACC | AGC | AAC | CAC | TGG | GTG | GTC | AAT | CCG | CGG | CAC |
| Asp | Ile | Thr | Ala | Thr | Ser | Asn | His | Trp | Val | Val | Asn | Pro | Arg | His |

|     | 828 |     |     | 837 |     |     | 846 |     |     | 855 |     | 864 |
| AAC | CTG | GGC | CTG | CAG | CTC | TCG | GTG | GAG | ACG | CTG | GAT | GGG | CAG | AGC |
| Asn | Leu | Gly | Leu | Gln | Leu | Ser | Val | Glu | Thr | Leu | Asp | Gly | Gln | Ser |

|     | 873 |     |     | 882 |     |     | 891 |     |     | 900 |     | 909 |
| ATC | AAC | CCC | AAG | TTG | GCG | GGC | CTG | ATT | GGG | CGG | CAC | GGG | CCC | CAG |
| Ile | Asn | Pro | Lys | Leu | Ala | Gly | Leu | Ile | Gly | Arg | His | Gly | Pro | Gln |

|     | 918 |     |     | 927 |     |     | 936 |     |     | 945 |     | 954 |
| AAC | AAG | CAG | CCC | TTC | ATG | GTG | GCT | TTC | TTC | AAG | GCC | ACG | GAG | GTC |
| Asn | Lys | Gln | Pro | Phe | MET | Val | Ala | Phe | Phe | Lys | Ala | Thr | Glu | Val |

|     | 963 |     |     | 972 |     |     | 981 |     |     | 990 |     | 999 |
| CAC | TTC | CGC | AGC | ATC | CGG | TCC | ACG | GGG | AGC | AAA | CAG | CGC | AGC | CAG |
| His | Phe | Arg | Ser | Ile | Arg | Ser | Thr | Gly | Ser | Lys | Gln | Arg | Ser | Gln |
|     |     |     |     |     |     |     |     |     |     |     |     |     |     | (300) |

|     | 1008 |     |     | 1017 |     |     | 1026 |     |     | 1035 |     | 1044 |
| AAC | CGC | TCC | AAG | ACG | CCC | AAG | AAC | CAG | GAA | GCC | CTG | CGG | ATG | GCC |
| Asn | Arg | Ser | Lys | Thr | Pro | Lys | <u>Asn</u> | <u>Gln</u> | <u>Glu</u> | <u>Ala</u> | <u>Leu</u> | <u>Arg</u> | MET | Ala |

|     | 1053 |     |     | 1062 |     |     | 1071 |     |     | 1080 |     | 1089 |
| AAC | GTG | GCA | GAG | AAC | AGC | AGC | GAC | CAG | AGG | CAG | GCC | TGT | AAG |
| Asn | Val | Ala | Glu | Asn | Ser | Ser | Ser | Asp | Gln | Arg | Gln | Ala | Cys | Lys |

|     | 1098 |     |     | 1107 |     |     | 1116 |     |     | 1125 |     | 1134 |
| AAG | CAC | GAG | CTG | TAT | GTC | AGC | TTC | CGA | GAC | CTG | GGC | TGG | CAG | GAC |
| Lys | <u>His</u> | <u>Glu</u> | <u>Leu</u> | <u>Tyr</u> | <u>Val</u> | <u>Ser</u> | <u>Phe</u> | Arg | Asp | Leu | Gly | Trp | Gln | Asp |

|     | 1143 |     |     | 1152 |     |     | 1161 |     |     | 1170 |     | 1179 |
| TGG | ATC | ATC | GCG | CCT | GAA | GGC | TAC | GCC | GCC | TAC | TAC | TGT | GAG | GGG |
| Trp | Ile | Ile | Ala | Pro | Glu | Gly | Tyr | Ala | Ala | Tyr | Tyr | Cys | Glu | Gly |

|     | 1188 |     |     | 1197 |     |     | 1206 |     |     | 1215 |     | 1224 |
| GAG | TGT | GCC | TTC | CCT | CTG | AAC | TCC | TAC | ATG | AAC | GCC | ACC | AAC | CAC |
| Glu | Cys | Ala | Phe | Pro | Leu | Asn | Ser | Tyr | MET | Asn | Ala | Thr | Asn | His |

TABLE IV-continued

```
        1233           1242           1251           1260           1269
GCC ATC GTG CAG ACG CTG GTC CAC TTC ATC AAC CCG GAA ACG GTG
Ala Ile Val Gln Thr Leu Val His Phe Ile Asn Pro Ile Ser Val 1278           1287           1296           1305           1314
CCC AAG CCC TGC TGT GCG CCC ACG CAG CTC AAT GCC ATC TCC GTC
Pro Lys Pro Cys Cys Ala Pro Thr Gln Leu Asn Ala Ile Ser Val 1323           1332           1341           1350           1359
CTC TAC TTC GAT GAC AGC TCC AAC GTC ATC CTG AAG AAA TAC AGA
Leu Tyr Phe Asp Asp Ser Ser Asn Val Ile Leu Lys Lys Tyr Arg 1368           1377           1386                    1399
AAC ATG GTG GTC CGG GCC TGT GGC TGC CAC     TAGCTCCTCC
Asn MET Val Val Arg Ala Cys Gly Cys His
                                      (431)

1409         1419         1429          1439          1448
    GAGAATTCAG   ACCCTTTGGG   GCCAAGTTTT   TCTGGATCCT   CCATTGCTC
```

When the tryptic sequence His-Glu-Leu-Tyr-Val-Ser-Phe-(ser) described above was identified, it was noted to be similar to the sequence His-Pro-Leu-Tyr-Val-Asp-Phe-Ser found in the bovine and human cartilage/bone protein BMP-2A sequence, for instance as described in co-pending U.S. application Ser. No. 179,100. Human BMP-7 shares homology with other BMP molecules as well as other members of the TGF-β superfamily of molecules. The cysteine-rich carboxy-terminal 102 amino acids residues of human BMP-7 shares the following homologies with BMP proteins disclosed in copending applications described above: 60% identity with BMP-2; 43% identity with BMP-3, 58% identity with BMP-4, 87% identity with BMP-6; and 88% identity with BMP-5. Human BMP-7 further shares the following homologies: 40% identity with TGF-β3; 40% identity with TGF-β2; 36% identity with TGF-β1; 29% identity with Mullerian Inhibiting Substance (MIS), a testicular glycoprotein that causes regression of the Mullerian duct during development of the male embryo; 25% identity with inhibin-α; 44% identity with inhibin-$β_B$; 45% identity with inhibin-$β_A$; 57% identity with Vgl, a Xenopus factor which may be involved in mesoderm induction in early embryogenesis [Lyons, et al., PNAS USA 86:4554-4558 (1989)]; and 58% identity with Dpp the product of the Drosophila decapentaplegic locus which is required for dorsal-ventral specification in early embryogenesis and is involved in various other developmental processes at later stages of development [Padgett, et al., Nature 325:81-84 (1987)].

The procedures described above and additional methods known to those skilled in the art may be employed to isolate other related proteins of interest by utilizing the bovine or human proteins as a probe source. Such other proteins may find similar utility in, inter alia, fracture repair, wound healing and tissue repair.

EXAMPLE VI

Expression of the BMP-7 Proteins

In order to produce bovine, human or other mammalian proteins of the invention, the DNA encoding it is transferred into an appropriate expression vector and introduced into mammalian cells or other preferred eukaryotic or prokaryotic hosts by conventional genetic engineering techniques. It is contemplated that the preferred expression system for biologically active recombinant human proteins of the invention will be stably transformed mammalian cells. It is further contemplated that the preferred mammalian cells will be CHO cells. The transformed host cell is cultured and the BMP-7 proteins expressed thereby are recovered and purified. The recombinantly expressed BMP-7 proteins are free of proteinaceous materials with which they are co-produced and with which they ordinarily are associated in nature.

In order to express biologically active human BMP-7 a selected host cell is transformed, using techniques known to those skilled in the art of genetic engineering, with a DNA sequence encoding human BMP-7 protein. The DNA comprises the nucleotide sequence from nucleotide #994 to #1389 set forth in Table IV encoding amino acid #300–#431. The DNA may comprise the DNA sequence from nucleotide #97 to #389 set forth in Table IV. The transformed host cells are cultured and the BMP-7 protein comprising the amino acid sequence from amino acid #300 to amino acid #431 as set forth in Table IV is expressed. The expressed protein is recovered, isolated and purified form the culture and culture medium. The purified protein is substantially free from other proteinaceous materials with which it is co-produced and from other contaminants.

One skilled in the art can construct mammalian expression vectors by employing the DNA sequences of the invention sequences and known vectors, such as pCD [Okayama et al., Mol. Cell Biol., 2:161–170 (1982)] and pJL3, pJL4 [Gough et al., EMBO J., 4:645–653 (1985)]. The transformation of these vectors into appropriate host cells may result in expression of the proteins of the invention. One skilled in the art could manipulate the sequences of the invention by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences there-from or altering nucleotides therein by other known techniques). The modified coding sequence could then be inserted into a known bacterial vector using procedures such as described in T. Taniguchi et al., Proc. Natl Acad. Sci. USA, 77:5230–5233 (1980). This exemplary bacterial vector could then be transformed into bacterial host cells and a protein of the invention expressed thereby. For a strategy for producing extracellular expression of a cartilage and/or bone protein of the invention in bacterial cells., see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a protein of the invention from mammalian cells involves the construction of cells containing multiple copies of the heterologous gene encoding proteins of the invention. The heterologous gene may be linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, J. Mol. Biol., 159:601-629 (1982). This approach can be employed with a number of different cell types.

For example, a plasmid containing a DNA sequence for a protein of the invention in operative association with other plasmid sequences enabling expression thereof and the DHFR expression plasmid pAdA26SV-(A)3 [Kaufman and Sharp, Mol. Cell. Biol., 2:1304 (1982)] may be co-introduced into DHFR-deficient CHO cells, DUKX-BII, by calcium phosphate coprecipitation and transfection, electroperation or protoplast fusion. DHFR expressing transformants are selected for growth in alpha media with dialyzed fetal calf serum, and subsequently selected for amplification by growth in increasing concentrations of MTX (sequential steps in 0.02, 0.2, 1.0 and 5 uM MTX) as described in Kaufman et al., Mol Cell Biol., 5:1750 (1983). Protein expression should increase with increasing levels of MTX resistance.

Transformants are cloned, and the proteins of the invention are recovered, isolated, and purified from the culture medium. Biologically active protein expression is monitored by the Rosen-modified Sampath-Reddi rat bone formation assay described above in Example III. Similar procedures can be followed to produce other related proteins.

EXAMPLE VII

Biological Activity of Expressed BMP-7 Proteins

To measure the biological activity of the expressed proteins obtained in Example VI above the BMP-7 proteins are recovered from the culture media and purified. BMP-7 may be partially purified on a Heparin Sepharose column and further purified using standard purification techniques known to those skilled in the art. 4 ml of the collected post transfection conditioned medium supernatant from one 100 mm culture dish is concentrated approximately 10 fold by ultrafiltration on a YM 10 membrane and then dialyzed against 20 mM Tris, 0.15 M NaCl, pH 7.4 (starting buffer). This material is then applied to a 1.1 ml Heparin Sepharose column in starting buffer. Unbound proteins are removed by an 8 ml wash of starting buffer, and bound proteins, including proteins of the invention, are desorbed by a 3-4 ml wash of 20 mM Tris, 2.0M NaCl, pH 7.4.

The proteins bound by the Heparin column are concentrated approximately 10-fold on a Centricon 10 and the salt reduced by diafiltration with 0.1% trifluoroacetic acid. The appropriate amount of this solution is mixed with 20 mg of rat matrix and then assayed for in vivo bone and/or cartilage formation activity by the Rosen-modified Sampath-Reddi assay. A mock transfection supernatant fractionation is used as a control.

The implants containing rat matrix to which specific amounts of human BMP-7 proteins of the invention have been added are removed from rats after approximately seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

Levels of activity may also be tested for host cell extracts. Purification is accomplished in a similar manner as described above except that 6M urea is included in all the buffers.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. An isolated and purified cDNA sequence encoding the BMP-7 protein of FIG. 4.

2. A purified cDNA sequence encoding a polypeptide having osteogenic properties, said cDNA sequence comprising at least the following nucleotide sequence encoding respectively the indicated amino acid sequence comprised within said osteogenic polypeptide:

```
AGC—CAG—AAC—CGC—TCC—AAG—ACG—CCC—AAG—AAC—CAG—GAA—GCC—CTG—CGG—
ser    gln    asn    arg    ser    lys    thr    pro    lys    asn    gln    glu    ala    leu    arg ATG—GCC—AAC—GTG—GCA—GAG—AAC—AGC—AGC—AGC—GAC—CAG—AGG—CAG—GCC—
met    ala    asn    val    ala    glu    asn    ser    ser    ser    asp    gln    arg    gln    ala TGT—AAG—AAG—CAC—GAG—CTG—TAT—GTC—AGC—TTC—CGA—GAC—CTG—GGC—TGG—
cys    lys    lys    his    glu    leu    tyr    val    ser    phe    arg    asp    leu    gly    trp CAG—GAC—TGG—ATC—ATC—GCG—CCT—GAA—GGC—TAC—GCC—GCC—TAC—TAC—TGT—
gln    asp    trp    ile    ile    ala    pro    glu    gly    tyr    ala    ala    tyr    tyr    cys GAG—GGG—GAG—TGT—GCC—TTC—CCT—CTG—AAC—TCC—TAC—ATG—AAC—GCC—ACC—
glu    gly    glu    cys    ala    phe    pro    leu    asn    ser    tyr    met    asn    ala    thr AAC—CAC—GCC—ATC—GTG—CAG—ACG—CTG—GTC—CAC—TTC—ATC—AAC—CCG—GAA—
asn    his    ala    ile    val    gln    thr    leu    val    his    phe    ile    asn    pro    glu

ACG—GTG—CCC—AAG—CCC—TGC—TGT—GCG—CCC—ACG—CAG—CTC—AAT—GCC—ATC—
```

-continued

```
thr——val——pro——lys——pro——cys——cys——ala——pro——thr——gln——leu——asn——ala——ile——

TCC—GTC—CTC—TAC—TTC—GAT—GAC—AGC—TCC—AAC—GTC—ATC—CTG—AAG—AAA—
ser——val——leu——tyr——phe——asp——asp——ser——ser——asn——val——ile——leu——lys——lys——

TAC—AGA—AAC—ATG—GTG—GTC—CGG—GCC—TGT—GGC—TGC—CAC—
tyr——arg——asn——met——val——val——arg——ala——cys——gly——cys——his——.
```

3. An isolated and purified cDNA sequence encoding a BMP-7 protein said DNA sequence comprising substantially the nucleotide sequence or a portion thereof selected from the group consisting of:
  (a) nucleotide #994 through nucleotide #1389 of FIG. 4;
  (2b) nucleotide #97 through nucleotide #1389 of FIG. 4; and
  (c) sequences which
    (1) hybridize to sequences (a) or (b) under stringent hybridization conditions; and
    (2) encode a protein characterized by the ability to induce the formation of cartridge and/or bone in the Rosen-modified Sampath-Reddi assay.

4. An isolated and purified cDNA sequence encoding a BMP-7 protein comprising the DNA sequence of FIG. 4 from nucleotide #994 to #1389.

5. An isolated and purified cDNA sequence encoding a BMP-7 protein said DNA sequence comprising nucleotide #97 through #1389 of FIG. 4.

6. The cDNA sequence of clone V2-5 having ATCC #68020.

7. A vector comprising the cDNA sequence of claim 1.

8. A vector comprising a cDNA sequence of claim 3 in operative association with an expression control sequence therefor.

9. A vector comprising the cDNA sequence of claim 4.

10. A vector comprising the cDNA sequence of claim 5 in operative association with an expression control sequence therefor.

11. A host cell transformed with a cDNA of claim 1.

12. A host cell transformed with a cDNA of claim 4.

13. A host cell transformed with a DNA sequence of claim 3.

14. A host cell transformed with the cDNA sequence of claim 10.

15. A method for producing a purified BMP-7 protein said method comprising the steps of
  (a) culturing in a suitable culture medium cells transformed with a DNA sequence comprising the cDNA sequence from nucleotide #97 to #1389 of FIG. 4; and
  (b) isolating and purifying said protein from said culture medium.

16. A method for producing a purified BMP-7 protein said method comprising the steps of
  (a) culturing in a suitable culture medium cells transformed with a DNA sequence comprising the cDNA sequence from nucleotide #994 to #1389 of FIG. 4; and
  (b) isolating and purifying said protein from said culture medium.

17. A method for producing a BMP-7 protein, said method comprising the steps of
  (a) culturing in a suitable culture medium said transformed host cell of claim 13; and
  (b) isolating and purifying said bone and/or cartilage inductive protein from said culture medium.

* * * * *